US010520475B2

(12) United States Patent
Su et al.

(10) Patent No.: US 10,520,475 B2
(45) Date of Patent: Dec. 31, 2019

(54) FIBER ACOUSTIC EMISSION SENSING APPARATUS AND METHOD FOR SERVICE BEHAVIOR OF HYDRAULIC CONCRETE STRUCTURE

(71) Applicant: Hohai University, Nanjing, Jiangsu (CN)

(72) Inventors: Huaizhi Su, Jiangsu (CN); Meng Yang, Jiangsu (CN); Chongshi Gu, Jiangsu (CN); Wei Xie, Jiangsu (CN)

(73) Assignee: Hohai University, Nanjing, Jiangsu (CN)

( * ) Notice: Subject to any disclaimer, the term of this patent is extended or adjusted under 35 U.S.C. 154(b) by 117 days.

(21) Appl. No.: 15/834,617

(22) Filed: Dec. 7, 2017

(65) Prior Publication Data
US 2019/0178850 A1 Jun. 13, 2019

(51) Int. Cl.
G01N 29/24 (2006.01)
G01N 29/14 (2006.01)
G01N 29/22 (2006.01)
G01D 5/353 (2006.01)
G01N 29/34 (2006.01)

(52) U.S. Cl.
CPC ..... *G01N 29/2418* (2013.01); *G01D 5/35335* (2013.01); *G01N 29/14* (2013.01); *G01N 29/225* (2013.01); *G01N 29/34* (2013.01); *G01D 5/35325* (2013.01); *G01D 5/35377* (2013.01); *G01N 2291/0232* (2013.01); *G01N 2291/102* (2013.01)

(58) Field of Classification Search
CPC .... G01N 29/2462; G01N 29/28; G01N 29/14; G01N 29/2418; G01N 29/225; G01N 29/34; G01N 29/2406; G01N 29/11; G01N 29/07; G01N 29/12; G01N 29/4427; G01H 9/004
See application file for complete search history.

(56) References Cited

U.S. PATENT DOCUMENTS

| 4,487,068 A | * | 12/1984 | Hawkins | G01N 29/14 73/159 |
| 5,381,695 A | * | 1/1995 | Payne | B23D 79/023 73/643 |
| 5,656,428 A | * | 8/1997 | McAllister | G01N 33/54373 204/193 |

(Continued)

*Primary Examiner* — Helen C Kwok
(74) *Attorney, Agent, or Firm* — Rankin, Hill & Clark LLP

(57) ABSTRACT

A fiber acoustic emission sensing apparatus and method including a laying device and an acoustic emission source; the laying device comprises base plate, first side plate and second side plate, the top portion of the first side plate connected with the top portion of the second side plate through an arc-shaped fiber-carrying channel, a main cavity formed by the first side plate and the second side plate; top portions of the first and second side plates respectively hinged with first and second arc-shaped covers, the lower end surface of the first arc-shaped cover fixedly connected with a first arc-shaped pressing body, the lower end surface of the second arc-shaped cover fixedly provided with a second arc-shaped pressing body, a first sensing fiber arranged under the first arc-shaped pressing body, and a second sensing fiber arranged under the second arc-shaped pressing body.

9 Claims, 2 Drawing Sheets

(56) References Cited

U.S. PATENT DOCUMENTS

| | | | | |
|---|---|---|---|---|
| 5,804,725 A | * | 9/1998 | Posakony | G01N 29/2462 73/590 |
| 2011/0288689 A1 | * | 11/2011 | Kageyama | A01G 7/00 700/284 |
| 2012/0103098 A1 | * | 5/2012 | Laugharn, Jr. | B01F 11/0283 73/644 |

* cited by examiner

FIBER ACOUSTIC EMISSION SENSING APPARATUS AND METHOD FOR SERVICE BEHAVIOR OF HYDRAULIC CONCRETE STRUCTURE

BACKGROUND

Since CORNING produced the first fiber with low loss, the fiber communication technology has been quickly developed, and various novel optical devices and photoelectric devices have also been continuously developed. At the moment, the fiber sensing technology started to sprout. In 1977, Naval Research Laboratory (NRL) started to implement the Foss plan (fiber sensor system) held by Dr. Charles M. Davis, and since then, the fiber sensor started to come out, and the following OTDR, BOTDA, FBG and other technologies were continuously proposed, and the fiber sensing technology got more and more attention and was widely utilized. However, the development of the fiber sensing technology to miniaturization, long distance, distribution structure and high precision is seriously obstructed due to low spatial discrimination, higher optical loss in large transmission distance and other factors.

When external factors like strain, temperature and load disturb the concrete structure, the interior of the material may have crack, deformation and other conditions, and at the moment, the structure may release elastic energy, i.e., acoustic emission. The acoustic emission technology in essence is to sense and collect these acoustic emission signals through using some acoustic emission sensors, and deduce the damage and break that are possible to existing in the structure through storing and discriminating these acoustic emission signals, so as to finally give the judgment to the service behavior of the concrete structure. The acoustic emission technology has the advantages of dynamic nature, sensibility and integrity, but the acoustic emission technology still has many defects, such as short signal transmission distance, little monitoring contents, bad anti-electromagnetic interference ability, etc. which seriously obstruct the development thereof.

Therefore, regarding to how to fuse the sensing fiber technology with the acoustic emission technology, make good for deficiency, and better increase the monitoring and detecting ability to the concrete structure, there are some introductions about the sensing fiber technology and the acoustic emission technique currently, but there are still many problems, which is basically the integration of FBG and the acoustic emission technology, but the integration of FBG and the acoustic emission technology cannot realize the distributed monitoring and detecting, and cannot fully bring each advantage into play. The integration of the distributed sensing fiber technology with the acoustic emission technology is rarer to be seen, and is helpless to the invisible or tiny structure damage in the concrete structure.

Therefore, it is necessary to develop a novel technology with the advantages of with high precision, high spatial resolution and remote monitoring, which integrates the novel distributed sensing fiber technology with the acoustic emission technology.

TECHNICAL FIELD

The present invention relates to a fiber acoustic emission sensing apparatus and method for a service behavior of a hydraulic concrete structure, and belongs to the field of concrete structure safety monitoring and detecting.

Wherein: 300 refers to first arc refers to shaped cover, 301 refers to second arc refers to shaped cover, 302 refers to left outer convex corner, 303 refers to right outer convex corner, 304 refers to first side plate, 305 refers to second side plate, 306 refers to common cavity circular hole, 307 refers to common cavity hexagonal hole, 308 refers to first arc-shaped pressing body, 309 refers to second arc-shaped pressing body, 310 refers to first arc-shaped fiber-carrying channel, 311 refers to second arc-shaped fiber-carrying channel, 312 refers to first sensing fiber, 313 refers to second sensing fiber, 314 refers to carrying path membrane, 315 refers to main common cavity, 316 refers to first external groove, 317 refers to second external groove, 318 refers to bottom external groove, 319 refers to laser optical source, 320 refers to mode-locked laser, 321 refers to polarization beam splitter, 322 refers to nonlinear amplifier, 323 refers to spectrograph, 324 refers to Michelson interferometer, 325 refers to femtosecond pulse, 326 refers to edge filter, 327 refers to first amplifier, 328 refers to optical splitter, 329 refers to concrete structure monitoring and evaluation system, 330 refers to memory, 331 refers to signal processor, 332 refers to second amplifier, 333 refers to optical detector, 334 refers to receiver, 335 refers to sensing fiber acoustic emission laying device, 336 refers to acoustic emission source, 337 refers to concrete structure and 338 refers to external load.

DETAILED DESCRIPTION

Figure 1:
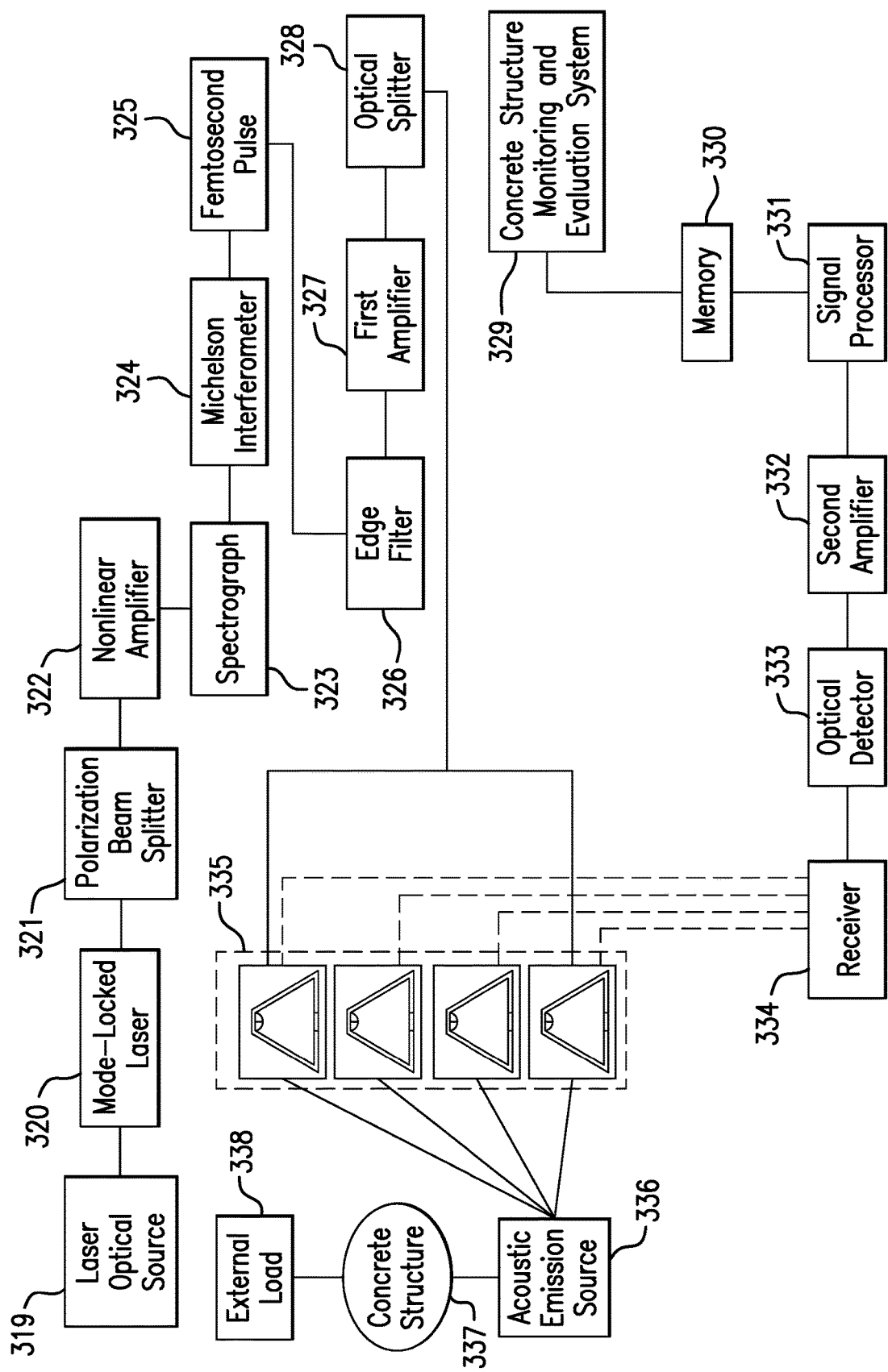
FIG. 1 is a structure diagram of the present invention.
Figure 2:
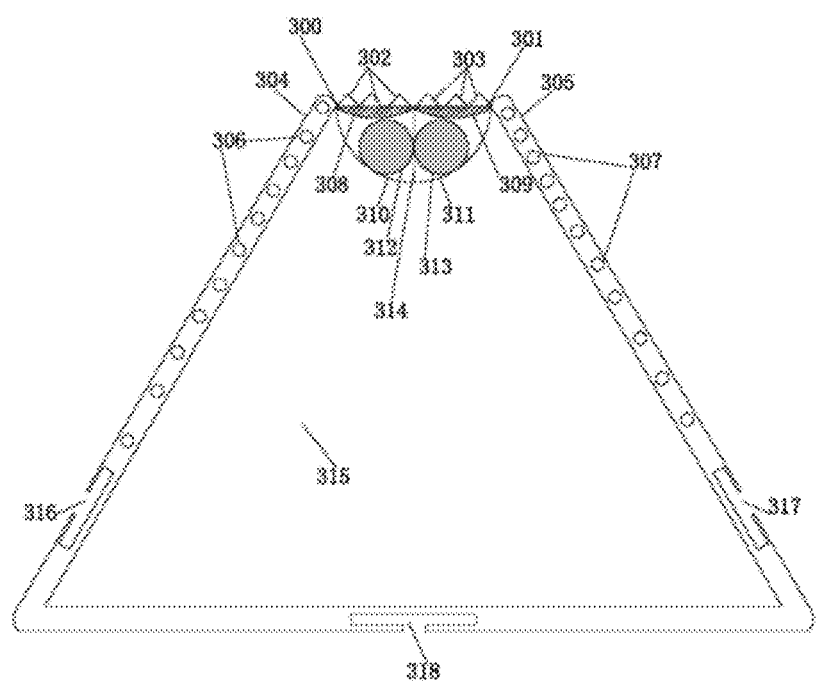
FIG. 2 is a structure diagram of a mobile apparatus in FIG. 1.

As shown in FIG. 1 and FIG. 2, in order to better describe the specific application of the present invention, the condition that the interior of the dam heel of some high concrete dam in China is possible to have cracks is specifically selected. A fiber acoustic emission sensing apparatus for a service behavior of a hydraulic concrete structure based on a sensing fiber acoustic emission technology is embedded in the dam heel of some high concrete dam, and the specific and actual engineering application of the apparatus is currently described in detail hereinafter.

A fiber acoustic emission sensing apparatus for a service behavior of a hydraulic concrete structure comprises a sensing fiber acoustic emission laying module, a sensing fiber module and an acoustic emission module, the sensing fiber module is connected with the acoustic emission module through an information system for concrete structure monitoring and evaluation, the sensing fiber acoustic emission laying module comprises four sensing fiber acoustic emission laying devices, each sensing fiber acoustic emission laying device is internally provided with a first GJJV tight-buffered sensing fiber 312 and a second GJJV tight-buffered sensing fiber 313, and the cracks of varying degrees may be formed in the dam heel of high concrete dam under the effect of water load, which cannot be found from the appearance. Therefore, the microscopic cracks which are possible to be formed in the interior need to be detected. Acoustic emission waves are transmitted to the first GJJV tight-buffered sensing fiber 312 and the second GJJV tight-buffered sensing fiber 313 in the sensing fiber acoustic emission laying module through an acoustic emission source 336 in the acoustic emission module, the first GJJV tight-buffered sensing fiber 312 and the second GJJV tight-buffered sensing fiber 313 are connected with the input end of a receiver 334 in the acoustic emission module, and are finally connected with an information system for concrete structure monitoring and evaluation 329 after passing through an optical detector 333, a second amplifier 332, a signal processor 331 and a memory 330 in sequence.

In the embodiment, a laser optical source 319 may emit a laser pulse, the output end of the laser optical source 319 is connected with the input end of a mode-locked laser 320, an ultra-short laser pulse may be generated by using a mode-locked technology, the width of the laser pulse is shortened to a femtosecond magnitude to generate a high pulse width and power value, the output end of the mode-locked laser 320 is connected with the input end of a polarization beam splitter 321, the output end of the polarization beam splitter 321 is connected with the input end of a nonlinear amplifier 322, the output end of the nonlinear amplifier 322 is connected with the input end of a spectrograph 323, the intensities at different wave length positions of a spectral line are detected through an optical detector such as a photomultiplier by using the spectrograph 323, the output end of the spectrograph 323 is connected with the input end of a Michelson interferometer 324, the femtosecond pulse outputted by the Michelson interferometer 324 enters the input end of a first amplifier 327 after passing through the input end of an edge filter 326, the output end of the first amplifier 327 is connected with the input end of a optical splitter 328, the output end of the polarization beam splitter 328 is connected with the input ends of the first sensing fiber 312 and the second sensing fiber 313 in the four sensing fiber acoustic emission laying devices.

In the embodiment, each sensing fiber acoustic emission laying device comprises a left outer convex corner 302 of an equilateral triangle with a side length of 2 cm, the first arc-shaped pressing body 308 with a radian of $\pi/3$, the first arc-shaped fiber-carrying channel 310 in an arc-shaped type with a radian of $\pi/2$ and a radius of 5 cm, the first GJJV tight-buffered sensing fiber 312, the common cavity circular hole 306 having a circular section with a diameter of 3 cm, the first side plate 304 with a length of 20 cm and width of 5 cm, the first arc-shaped cover 300 with a length of 5 cm and a width of 1 cm, the first external groove 316 with an opening groove depth of 2 cm and a width of 4 cm, the second arc-shaped cover 301 with a length of 5 cm and a width of 1 cm, the right outer convex corner 303 of the equilateral triangle with a side length of 2 cm, the second side plate 305 with a length of 20 cm and a width of 5 cm, the common cavity hexagonal hole 307 having an equilateral hexagonal section with a side length of 1 cm, the second external groove 317 with an opening having a depth of 2 cm and a width of 4 cm, the second arc-shaped pressing body 309 with a radian of $\pi/3$, the second arc-shaped fiber-carrying channel 311 in an arc-shaped type with a radian of $\pi/2$ and a radius of 5 cm, the second GJJV tight-buffered sensing fiber 313, and the bottom external groove 318 having an opening with a height of 1 cm and a width of 5 cm. The first arc-shaped cover 300 is connected with the second arc-shaped cover 301 through a locking device, wherein the locking device may either be a connecting piece like a screw and a bolt, or be a snap. The first GJJV tight-buffered sensing fiber 312 and the second GJJV tight-buffered sensing fiber 313 are placed in the first arc-shaped fiber-carrying channel 310 in an arc-shaped type with a radian of $\pi/2$ and a radius of 5 cm and the second arc-shaped fiber-carrying channel 311 in an arc-shaped type with a radian of $\pi/2$ and a radius of 5 cm, the first arc-shaped pressing body 308 with a radian of $\pi/3$ and the second arc-shaped pressing body 309 with a radian of $\pi/3$ are respectively connected with the first arc-shaped fiber-carrying channel 310 and the second arc-shaped fiber-carrying channel 311, the common cavity circular hole 306 and the common cavity hexagonal hole 307 are respectively laid on the first side plate 304 and the second side plate 305, the first side plate 304 and the second side plate 305 are respectively connected with the first arc-shaped fiber-carrying channel 310 and the second arc-shaped fiber-carrying channel 311, the carrying-channel membrane is located between the second arc-shaped fiber-carrying channel 311 in an arc-shaped type with a radian of $\pi/2$ and a radius of 5 cm and the first arc-shaped fiber-carrying channel 310 in an arc-shaped type with a radian of $\pi/2$ and a radius of 5 cm, the main common cavity 315 is formed between the first side plate 304 with a length of 20 cm and a width of 5 cm and the second side plate 305 with a length of 20 cm and a width of 5 cm, and the sensing fiber acoustic emission laying device is installed in the structure to be monitored through the first external groove 316 with an opening having a height of 2 cm and a width of 4 cm, the second external groove 317 having an opening with a height of 2 cm and a width of 4 cm and the bottom external groove 318 having an opening with a height of 1 cm and a width of 5 cm.

In the embodiment, when the elevation of water surface is 100 m, cracks of different degrees and different lengths may be formed in the dam heel of the high concrete dam under the effect of 100 m head pressure; at the moment, the cracks with different lengths may stimulate to generate the acoustic emission source 336, the optical information of the first GJJV tight-buffered sensing fiber 312 and the second GJJV tight-buffered sensing fiber 313 laid in the four sensing fiber acoustic emission laying devices of the concrete structure may be continuously changed with the acoustic emission waved generated by the acoustic emission source 336, the optical signal output ends of the first sensing fiber 312 and the second sensing fiber 313 are connected with the input end of the receiver 334, the output end of the receiver 334 is connected with the input end of the optical detector 333, the output end of the optical detector 333 is connected with the input end of the second amplifier 332, the output end of the second amplifier 332 is connected with the input end of the signal processor 331, the output end of the signal processor 331 is connected with the input end of the memory 330, the optical information on the first sensing fiber 312 and the second sensing fiber 313 continuously changed with the change of the acoustic emission waves is saved in real time through the memory 330, and the optical information is continuously outputted in the information system for concrete structure monitoring and evaluation 329.

A method of the fiber acoustic emission sensing apparatus for a service behavior of a hydraulic concrete structure comprises the following steps.

(1) Determine the Length of the Sensing Fiber in the Sensing Fiber Acoustic Emission Laying Device Regarding to the dam heel of the high concrete dam under the effect of 100 m head pressure, the enhancement of monitoring in strength and intensity shall be considered. Therefore, 8 pieces of GJJV tight-buffered sensing fibers with a length 500 m are selected as the first GJJV tight-buffered sensing fiber 312 and the second GJJV tight-buffered sensing fiber 313 in the four sensing fiber acoustic emission laying devices.

(2) Configure the Sensing Fiber Acoustic Emission Laying Device to the Area of the Structure to be Monitored The first side plate 304 with a length of 20 cm and a width of 5 cm and the second side plate 305 with a length of 20 cm and a width of 5 cm are laid at a 60-degree included angle with a horizontal plane to form the main common cavity 315, the first sensing fiber 312 and the second sensing fiber 313 are placed in the first arc-shaped fiber-carrying channel 310 and the second arc-shaped fiber-carrying channel 311, the first arc-shaped cover 300 with a length of 5 cm and a width of 1 cm and the second arc-shaped cover 301 with a length of 5 cm and a width of 1 cm are rotated to press the first arc-shaped pressing body 308 with a radian of π/3 and the second arc-shaped pressing body 309 with a radian of π/3 in the first arc-shaped fiber-carrying channel 310 and the second arc-shaped fiber-carrying channel 311 in an arc-shaped type with a radian of π/2 and a radius of 5 cm in which the first sensing fiber 312 and the second sensing fiber 313 are contained.

(3) Configure Members in the Sensing Fiber Module and the Acoustic Emission Module The sensing fiber module is assembled according to the order of the laser optical source 319, the mode-locked laser 320, the polarization beam splitter 321, the nonlinear amplifier 322, the spectrograph 323, the Michelson interferometer 324, the edge filter 326, the first amplifier 327 and the optical splitter 328 in sequence, then the acoustic emission module is assembled according to the order of the receiver 334, the optical detector 333, the second amplifier 332, the signal processor 331 and the memory 330, then each member is opened and debugged to check the running state of each member.

(4) Turn on Each Switch to Conduct Monitoring and Detecting

Each switch is firstly turned on under the initial condition, the numerical value of the optical information of the first GJJV tight-buffered sensing fiber 312 and the second GJJV tight-buffered sensing fiber 313 in the four sensing fiber acoustic emission laying devices under the initial state is obtained as the initial value, and the initial interference-free processing may be conducted to the subsequent result value through subtracting the initial value. When cracks or structure damages in other forms are generated in the dam heel of the engineering, acoustic emission waves resonate with the common cavity circular hole 306, the common cavity hexagonal hole 307 and the main common cavity 305 in different time and frequencies; therefore, the information will be secondarily amplified and delayed in physical size; different acoustic emission information may be transmitted to the first sensing fiber 312 and the second sensing fiber 313, so as to detect and monitor the dam heel through detecting the change of the optical information of the first sensing fiber 312 and the second sensing fiber 313.

The description above is only the preferable embodiment of the present invention, and it should be noted that those skilled in the art may make a plurality of improvements and decorations without departing from the principle of the present invention, and these improvements and decorations shall also fall within the protection scope of the present invention.

The invention claimed is:

1. A fiber acoustic emission sensing apparatus for a service behavior of a hydraulic concrete structure, comprising a plurality of sensing fiber emission laying devices and an acoustic emission source, wherein each sensing fiber emission laying device comprises a base plate, and a first side plate and a second side plate fixedly connected with two sides of the base plate, a top portion of the first side plate is connected with a top portion of the second side plate through an arc-shaped fiber-carrying channel, and a main common cavity is formed by the base plate, the first side plate, the second side plate and the arc-shaped fiber-carrying channel; the top portions of the first side plate and the second side plate are respectively hinged with a first arc-shaped cover and a second arc-shaped cover, a lower end surface of the first arc-shaped cover is fixedly connected with a first arc-shaped pressing body, a lower end surface of the second arc-shaped cover is fixedly provided with a second arc-shaped pressing body, a first sensing fiber in the arc-shaped fiber-carrying channel is arranged under the first arc-shaped pressing body, and a second sensing fiber is arranged under the second arc-shaped pressing body, and the first arc-shaped cover is connected with the second arc-shaped cover through a locking device; after the first arc-shaped cover and the second arc-shaped cover are rotated to tightly press the first sensing fiber and the second sensing fiber through the first arc-shaped pressing body and the second arc-shaped pressing body, the first arc-shaped cover and the second arc-shaped cover are locked through the locking device; and the acoustic emission source is connected with one end of the first sensing fiber and one end of the second sensing fiber, other ends of the first sensing fiber and the second sensing fiber are connected with a receiver, and the receiver is connected with an optical detector, a second amplifier, a signal processor, a memory and an information system for concrete structure monitoring and evaluation in sequence.

2. The fiber acoustic emission sensing apparatus for a service behavior of a hydraulic concrete structure according to claim 1, further comprising a laser optical source, wherein the laser optical source passes through a mode-locked laser, a polarization beam splitter, a nonlinear amplifier, a spectrograph, a Michelson interferometer, a femtosecond pulse, an edge filter and a first amplifier in sequence to be connected with an optical splitter, and the optical splitter is connected with the first sensing fiber and the second sensing fiber.

3. The fiber acoustic emission sensing apparatus for a service behavior of a hydraulic concrete structure according to claim 1, wherein a plurality of first through holes is arranged on the first side plate along an axis direction of the first sensing fiber.

4. The fiber acoustic emission sensing apparatus for a service behavior of a hydraulic concrete structure according to claim 3, wherein a plurality of second through holes is arranged on the second side plate along an axis direction of the second sensing fiber.

5. The fiber acoustic emission sensing apparatus for a service behavior of a hydraulic concrete structure according to claim 4, wherein the first through hole is a common cavity circular hole, a section of the common cavity circular hole is a circular hole, the second through hole is a common cavity hexagonal hole, a section of the common cavity hexagonal hole is a hexagonal hole, and both the first through hole and the second through hole are in an odd number.

6. The fiber acoustic emission sensing apparatus for a service behavior of a hydraulic concrete structure according to claim 5, wherein both the first arc-shaped cover and the second arc-shaped cover are provided with a convex corner.

7. The fiber acoustic emission sensing apparatus for a service behavior of a hydraulic concrete structure according to claim 6, wherein external surfaces of the base plate, the first side plate and the second side plate are all provided with an external groove.

8. The fiber acoustic emission sensing apparatus for a service behavior of a hydraulic concrete structure according to claim 7, wherein the first sensing fiber and the second sensing fiber are separated by a carrying-channel membrane.

9. A method of a fiber acoustic emission sensing apparatus for a service behavior of a hydraulic concrete structure, comprising the following steps of:

first step: establishing each component in a sensing fiber acoustic emission laying module, equipping a sensing fiber with a certain length, rotating a first side plate and a second side plate to form a 60-degree included angle with a horizontal plane, so as to form a main common cavity;

second step: rotating a first arc-shaped cover and a second arc-shaped cover to drive a first arc-shaped pressing body and a second arc-shaped pressing body to move, respectively pressing a first sensing fiber and a second sensing fiber in the arc-shaped fiber-carrying channel through a bulge between the first arc-shaped pressing body and the second arc-shaped pressing body, and laying four sensing fiber acoustic emission laying devices in a concrete structure to be tested by external grooves;

third step: opening and debugging each sensing fiber acoustic emission laying device, adjusting and marking the first sensing fiber and the second sensing fiber in the four sensing fiber acoustic emission laying devices laid in the concrete structure, and modulating femtosecond pulses of the first sensing fiber and the second sensing fiber through a laser optical source;

fourth step: femtosecond pulse optical information of the first sensing fiber and the second sensing fiber in the four sensing fiber acoustic emission laying devices being affected by acoustic emission waves in an acoustic emission source when the concrete structure generates the acoustic emission source under the effect of an external load, and the acoustic emission waves resonating with a common cavity circular hole, a common cavity hexagonal hole and a main common cavity in different time and frequencies, the femtosecond pulse optical information being secondarily amplified and delayed in physical size, and secondarily amplified and delayed femtosecond pulse optical information being transferred to the first sensing fiber and the second sensing fiber;

fifth step: receiving and detecting varying femtosecond pulse optical information through the receiver and the optical detector, and then conducting de-noising processing and data storage on the varying femtosecond pulse optical information through the signal processor and the memory, so as to collect the varying femtosecond pulse optical information in an information system for concrete structure monitoring and evaluation; and sixth step: drawing a varying time-history curve of the varying femtosecond pulse optical information in the information system for concrete structure monitoring and evaluation to reflect a change of the acoustic emission waves generated by the acoustic emission source, so as to dynamically monitor and detect the concrete structure.

* * * * *